US 7,359,056 B2

(12) United States Patent
Koshinz

(10) Patent No.: US 7,359,056 B2
(45) Date of Patent: Apr. 15, 2008

(54) ENHANCED SIGNAL DETECTION OF OPTICALLY ENCODED PARTICLES VIA FLARE

(75) Inventor: Dennis G. Koshinz, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 212 days.

(21) Appl. No.: 11/131,171

(22) Filed: May 17, 2005

(65) Prior Publication Data

US 2007/0035730 A1   Feb. 15, 2007

(51) Int. Cl.
*G01N 21/49* (2006.01)
(52) U.S. Cl. ...................... 356/446; 356/437
(58) Field of Classification Search ........ 356/445–448, 356/437–439
See application file for complete search history.

(56) References Cited

U.S. PATENT DOCUMENTS

| | | |
|---|---|---|
| 3,831,318 A | 8/1974 | Richmond |
| 4,102,138 A | 7/1978 | Dreker et al. |
| 4,121,790 A | 10/1978 | Graham |
| 4,899,962 A | 2/1990 | Mueller |
| 5,188,186 A | 2/1993 | Nash |
| 5,538,781 A | 7/1996 | Rao et al. |
| 2005/0024634 A1* | 2/2005 | Barker et al. ............... 356/301 |

OTHER PUBLICATIONS

Cunin et al, "Biomolecular screening with encoded porous-silicon photonic crystals", Nature Materials, vol. 1, Sep. 2002, pp. 39-41.*
Johnson, S. G. (2003). Photonic crystals: periodic surprises in electromagnetism. *One-week seminar (five ½hour lectures) MIT MRS Chapter, 2003 IAP tutorial series.* http://ab-initio.mit.edu/photons/tutorial/ (Oct. 6, 2005).
Chemical impact: fireworks., *HM chem general chemistry online.* http://www.hmchemdemo.clt.binghamton.edu/zumdahl/docs/chemistry/07atomstructure/library.../ (Nov. 30, 2004).
(Sep. 7, 2004). Pyrotechnics. *Hummel Croton Inc.* http://www.hummelcroton.com/main/pyro.html (Nov. 30, 2004).

(Continued)

*Primary Examiner*—Richard A. Rosenberger
(74) *Attorney, Agent, or Firm*—Harness, Dickey & Pierce, P.L.C.

(57) ABSTRACT

Methods of, and systems for, detecting an airborne material. In a first preferred embodiment, a method is provided that includes deploying a cloud of optical sensors, illuminating at least a portion of the cloud with a flare, and detecting the cloud using the illumination provided by the flare. Preferably, the illumination is in the infrared, near infrared, or visible spectral range. Also, the sensors can be porous silicon sensors for measuring the concentration of either a chemical or biological agent. Moreover, the method may include deploying the flare while remaining concealed. Preferably, the spectrum of the flare is compared with the spectrum from the cloud of sensors.

13 Claims, 4 Drawing Sheets

OTHER PUBLICATIONS

Bryden Dr. W. Threat agent cloud tactical intercept & countermeasure (TACTIC). http://www.darpa.gov/spo/programs/tactic.htm (Oct. 29, 2004).

Sailor M. Silicon gets sensitive. Archives special focus section. http://oemagazine.com/fromTheMagazine/mar03/silicon.html (Oct. 29, 2004).

Pavesi L., Mulloni V (2000). Electrochemically oxidised porous silicon microcavities. *Materials science and engineering B69-70* (2000) 59-65. www.elsevier.com/locate/mseb.

Luu-19 flare. *FAS military analysis network.* http://www.fas.org/man/dod-101/sys/dumb/luu19.htm (Nov. 1, 2004).

Li, Y., Cunin, F., Link J., Gao, T., Betts, R., Reiver, S., Chin, V., Bhatia, S., Sailor, M. (2003). Polymer replicas of photonic porous silicon for sensing and drug delivery applications. *Research Articles (Science vol. 229)*. http://www.sciencemag.org (Mar. 28, 2003).

Porous silicon based biosensors. *Faculty of science & engineering school of chemistry, physics & earth sciences.* http://www.scieng.flinders.edu.au/cpes/people/voelcker_n.html_files/biosensors.html. (Feb. 2, 2006).

Airbags may bounce back to mars (2000). *Red planet rebound—airbags to cushion mars landing.* http://www.space.com/scienceastronomy/solarsystem/mars_airbags_000707.html (Mar. 1, 2006).

Liquid body armor in the works (2004). *CBS news scitech.* http://www.cbsnews.com/stories/2004/04/30/tech/main614961.shtml (Jan. 24, 2005).

Swarts, D. (2002). How airfence works. *Roadracing world action fund roadracing & motorcycle technology.* http://actionfund.roadracingworld.com/News/Article/?ARTICLE_ID=191 (Feb. 6, 2006).

Temporary water-inflated portable dams for construction worksite dewatering reusable cofferdams, flood control products and flood barriers. *Aqua-Berriers water-inflated dams.* http://www.aquabarrier.com/ (Feb. 6, 2006).

USCD researchers fabricate tiny "smart dust" particles capable of detecting bioterrorist and chemical agents. *University of California, San Diego science & engineering press release.* http://ucsdnews.ucsd.edu/newsrel/science/mcsmartdust.htm (Feb. 6, 2006).

Targeted smart dust how it works. *UCSD Sailor Research Group, University of California, San Diego department of chemistry and biochemistry.* http://chem-faculty.ucsd.edu/sailor/research/smartdust.htm (Feb. 6, 2006).

\* cited by examiner

ENHANCED SIGNAL DETECTION OF OPTICALLY ENCODED PARTICLES VIA FLARE

REFERENCE TO RELATED APPLICATIONS

This application is related to and incorporates by reference U.S. patent application Ser. No. 11/131,173 entitled Co-Deployed Optical Referencing For Responsive Dust-Based Sensing System, and filed by Hager et al. on May 17, 2005.

FIELD

This disclosure relates generally to methods and apparatus for illuminating optical detectors and, more particularly, methods and apparatus for illuminating clouds of porous silicon optical sensors that are used to detect airborne chemicals.

BACKGROUND OF THE INVENTION

Clouds of pollution and other airborne materials are difficult to detect. Yet the concentration of these materials needs to be measured to enable those near the cloud to respond in an appropriate manner. Without an accurate assessment of the strength of the cloud unnecessary evacuations may be ordered or a needed evacuation may not be deemed necessary. The materials that can occur in these clouds include man-made pollution (e.g. a release from a chemical plant), natural pollution (e.g. volcanic fumes), and chemical and biological warfare agents. The difficulty of detecting these clouds arise for several reasons. First, the materials may be invisible and otherwise undetectable by human beings even at concentration levels that pose an immediate health threat. Second, the clouds tend to move with the wind so that, once released, they can travel long distances, thereby appearing without warning. Further, drafts, inversions, and other thermal gradients can cause the cloud to concentrate in some geographic areas (e.g. valleys) while dispersing rapidly from other areas (e.g. hilltops). Similarly, the cloud might be found at some altitudes and not found at others. Also, because these clouds might be found at some height above the ground, it may not be possible to place an instrument in the cloud short of flying a probe into the cloud. The clouds may also have irregular shapes with ill-defined boundaries (i.e. the cloud boundary may be marked by either a sharp or gradual concentration gradient or some combination of the two). Thus, where a particular cloud might be found is subject to a number of vagaries that cause difficulties in predicting where the cloud might exist.

BACKGROUND

One solution to these problems is to deploy a cloud of minute optical sensors into the suspected location(s) of the clouds. These clouds of minute sensors are sometimes referred to as "responsive dust." Recently, porous silicon optical sensors have become available for this application. Each of these sensors is manufactured from silicon that has been etched to create a porous surface. The etching process is tailored to create pores of a size, depth and number to enable the sensors to selectively bind to a particular, pre-selected material. When the sensors encounter that particular material, the material reacts with the silicon of the sensor. By various mechanisms that depend on the particular material involved, the reflectance spectrum of the silicon changes as a result of the reaction. Thus, observing the reflectance spectrum of the sensors yields a measure of the amount of the material that the sensors have encountered.

SUMMARY

Observing the reflectance spectrum of optical sensors to measure the amount of a material encountered by the sensor suffers from several problems. First, the electromagnetic energy ("light") source and the detector that is used to measure the reflectance spectrum must be initially aligned and held in strict alignment during the measurement process. Maintaining the alignment can be quite difficult because, at times, either the source, sensor cloud, or detector will move relative to one and other. Also, environmental factors along the path that the light travels from the source, to the sensors, and then to the detector may cause an attenuation of the light at some of the frequencies that the sensor attenuates reflected light. As a result, when the light arrives at the detector from the sensor, it is difficult to ascertain whether the attenuation of the light was caused by the sensor's exposure to the material or due to the environmental factors. It is in view of the above problems that the present disclosure was developed. The disclosure provides methods and apparatus for illuminating a cloud of optical sensors that are tailored to measure the concentration of an airborne material.

In a first embodiment, a method is provided that includes deploying a cloud of optical sensors, illuminating at least a portion of the cloud with a flare, and detecting the cloud using the illumination provided by the flare. Preferably, the illumination is in the infrared, near infrared, or visible spectral range. Also, the sensors can be porous silicon sensors that are used for measuring the concentration of either a chemical or biological agent. Moreover, the method may include deploying the flare while remaining concealed. Preferably, the spectrum of the flare is compared with the spectrum from the cloud of sensors.

In a second embodiment, the present disclosure provides a system for detecting the presence of an airborne material. The system includes a plurality of optical sensors and a flare. In operation, the flare illuminates the plurality of sensors that have a reflectivity dependent upon whether the material is present at the sensor. Preferably, the system includes a detector that detects the sensors (or a cloud of the sensors). Also, the system may include an aircraft, artillery shell, or other device for deploying the flare.

Further features and advantages as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate exemplary embodiments of the present disclosure and together with the description, serve to explain the principles of the disclosure. In the drawings.

DETAILED DESCRIPTION

Figure 1:
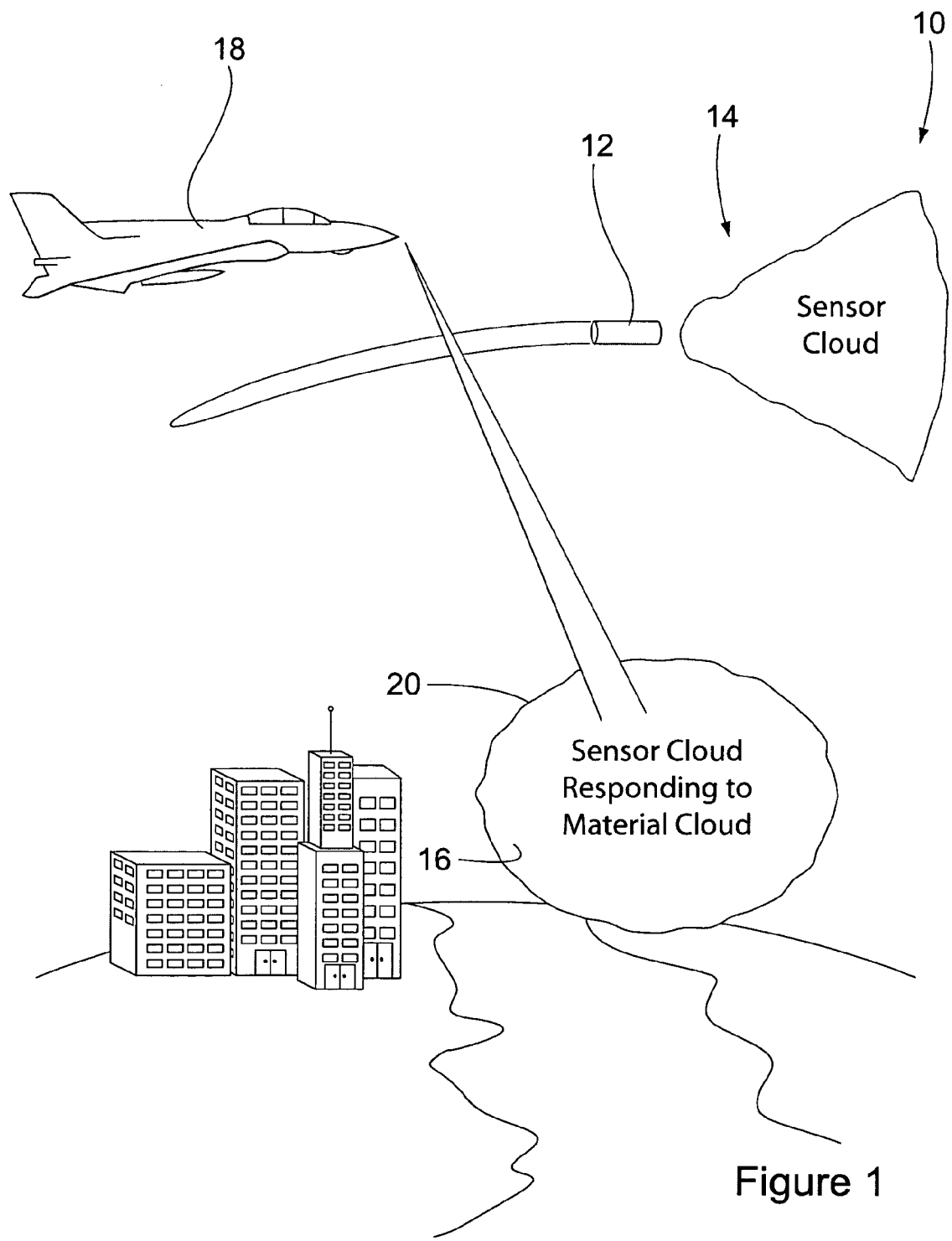
FIG. 1 illustrates an airborne material measuring system constructed in accordance with the principles of the present disclosure.

Referring to the accompanying drawings in which like reference numbers indicate like elements, FIG. 1 illustrates a system 10 constructed in accordance with the principles of the present disclosure.

The system 10 of FIG. 1 includes a deployment mechanism, two clouds 14 and 16 of optical sensors, and a vehicle 18 that includes an optical detector. Also, FIG. 1 shows a cloud 20 of airborne material that can be, for example, a pollutant, a chemical or biological agent, or other impurity in the air. The cloud 16 of sensors is shown, at least partly, as being coincident with the cloud of material 20 whereas the cloud 14 of sensors is shown being spaced apart from the cloud 20. Where the sensors of the cloud 16 are in contact with the material cloud 20 the material reacts with the porous silicon and causes the sensors to reflect a different spectrum than the spectrum reflected by the sensors in the unaffected sensor cloud 14.

In operation, deployment mechanisms 12 are positioned to deploy the cloud of sensors 14 and 16 at locations where a cloud 20 of material may be present. The deployment mechanisms then deploy the sensors as the clouds 14 and 16. Where the deployment mechanism 12 is an artillery shell (as shown), a fuse ignites a small charge of explosive material that propels the sensors from the shell to form the cloud 14 or 16. If the material cloud 20 is present where the sensors drift, the sensors react with the material and begin reflecting the altered spectrum (i.e. the sensors change color). The detector onboard the vehicle 18 is then pointed toward the clouds 14 and 16 of sensors to detect, and preferably record, the reflected spectrum. Since the amount of attenuation is related to the concentration of material in the cloud 20, the system 10 measures the concentration of the cloud 20.

Figure 2:
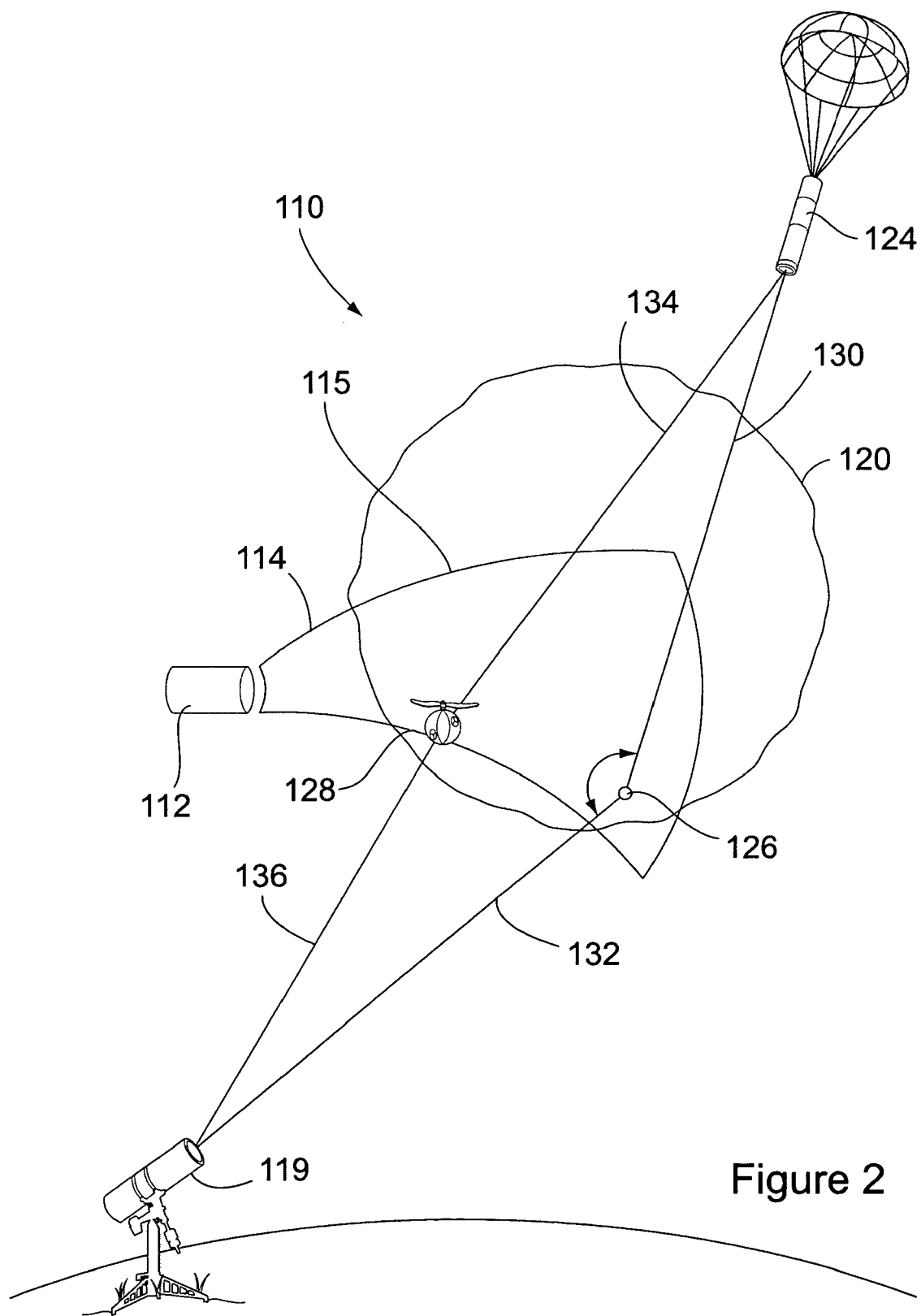
FIG. 2 illustrates a system of an embodiment of the present disclosure.

Turning now to FIG. 2, another exemplary system 110 that is provided by the present disclosure is illustrated. The system 110 differs from the system 10 of FIG. 1 in that FIG. 2 shows only one cloud 114 of sensors including a portion 115 that overlaps the material cloud 120. FIG. 2 also shows a detector 119, an illumination source 124, an individual sensor 126, an optical reference 128, and the paths 130, 132, 134, and 136 between the components of the system 110. The detector 119 can be any device capable of detecting the reflectance spectrum of the sensor 126 and is, preferably, a charge coupled device (CCD) having infrared, near infrared, and visible detection capabilities. The source 124 is a flare with a parachute to prolong its descent through the air. Unlike lasers, spotlights, and strobes, the flare 124 does not require electricity. Nor does the flare 124 require being set up or aligned with the detector 119 and the sensor 126. The flare 124 radiates electromagnetic energy (across an appropriate range of wavelengths) toward the sensor cloud 114 and more particularly toward the sensor 126. The sensor 126 reflects the electromagnetic energy ("light") toward the detector 119 and can be a porous silicon sensor with a porosity tailored for sensitivity to a pre-selected material. In the alternative, the sensor 126 can be a MEMS device or even one of the many sensors in a cloud of "smart dust." In any case, the reflectance of the sensor 126 varies depending on the presence of the material at the sensor 126. In contrast, the reference 128 has a reflectance that varies in a pre-selected manner (e.g. oscillates) between a high value and a low value thereby enabling an observer or detector 119 to discriminate between the reference 128, objects in the environment, and the preferred smart dust sensors 126.

As discussed in J. R. Link and M. J. Sailor, Proc. Nat Acad. Sci. 2003 100, 10607-10610 (see also http://chem-faculty.ucsd.edu/sailor/research/smartdust.html), "smart dust" is prepared in a two-step process. In the first step, a porous photonic structure is produced by etching silicon with an electrochemical machining process. This step imparts a highly reflective and specific color-code to the material that acts like an address, or identifying bar-code for the particles. The second step involves chemically modifying the porous silicon photonic structure so that it will find and stick to the desired target material. The two steps (etch and modify) are repeated with a different color and a different chemistry, yielding films having one side with one color (e.g., red) and the other side with another color (e.g., green). The films are broken up into particles about the size of a human hair and then deployed. Once deployed, the particles of the porous silicon photonic structure seek out and attach themselves to particles or droplets of the target material, presenting one surface (e.g., the red surface) to the outside world and the other (e.g., green) surface towards the inside of the particle or droplet.

Once they find the material for which they were programmed, the individual optical sensors (i.e., the smart dust particles) begin to line up, or "tile" themselves on the surface of the target droplet. The optical properties of the tiled particle combine to give a mirror whose characteristic color is easily observed. This collective behavior provides a means of amplifying the molecular recognition event that occurs at the surface of each individual target particle. As a means of signaling their presence at the target droplet, the smart dust particles change color in a predictable fashion. As the nanostructure comes in contact with the target material, some of the liquid from the target is absorbed into it. The liquid wicks into the regions of the nanostructure that have been modified with the appropriate chemistry. Thus, the presence of the target material in the nanostructure causes a predictable change in the color code, signaling to the outside observer that the correct target material has been located.

In a preferred embodiment, these nano-structured "smart dust" chemical (or biological agent) sensors use no power, are the size of dust particles, and can be probed at a remote distance using visible or infrared laser technology. Nanoscale holes in the porous silicon matrix act as concentrators, condensing vapors of the analyte. Catalytic reactions take place in small micellar nano-reactors in the porous silicon, converting the target material (if present in the analyte) into a chemical that can be recognized specifically by the matrix, thereby causing a signal that scales with dose in the from of a predictable color change. For additional information the reader is referred to T. A. Schmedake, F. Cunin, J. R. Link, and M. J. Sailor, Adv. Mater. 2002, 14, 1270-1272, and J. Am. Chem. Soc. 2000, (22), 5399-5400), and University of California, San Diego, "UCSD RESEARCHERS FABRICATE TINY 'SMART DUST' PARTICLES CAPABLE OF DETECTING BIOTERRORIST AND CHEMICAL AGENTS," Sep. 2, 2002-Viewed Online Feb. 8, 2005 at see also http://ucsdnews.ucsd.edu/newsrel/science/mcsmartdust.htm.

Light from the flare 124 illuminates the volume of air (an "area") that is suspected of containing the material cloud 120. Because the sensor cloud 114 has been deployed in that vicinity, light travels along path 130 from the flare 124 to at least some of the sensors 126. Depending on the concentration of material sensed by the sensors 126, the light is attenuated by an amount at predictable wavelengths by the sensors 126. The attenuated light from at least some of the illuminated sensors 126 then travels along the path 132 to the detector 119 where the concentration is detected remotely.

In many cases, it is possible to detect the material cloud 120 from a great distance. However, attenuation and scattering of the light along the paths 130 and 132 may alter the light arriving at the detector 119. Further, it is possible that the environmental attenuation (that occurs along the paths 130 and 132) might be at those wavelengths affected by the sensor's 126 contact with the material of the cloud 120. Thus, it might be unclear whether the attenuation of the light (as received at the detector 119) is due to the sensor 126 or environmental factors along the paths 130 and 132. Accordingly, the reference 128 can be co-deployed with the sensor cloud 120 to provide a reference signal for calibrating the detector 119. Such a reference is described in U.S. patent application Ser. No. 11/131,173, entitled Co-Deployed Optical Referencing For Responsive Dust-Based Sensing System, and filed by Hager et al. on May 17, 2005 which is incorporated by reference as if set forth in full.

Figure 3:
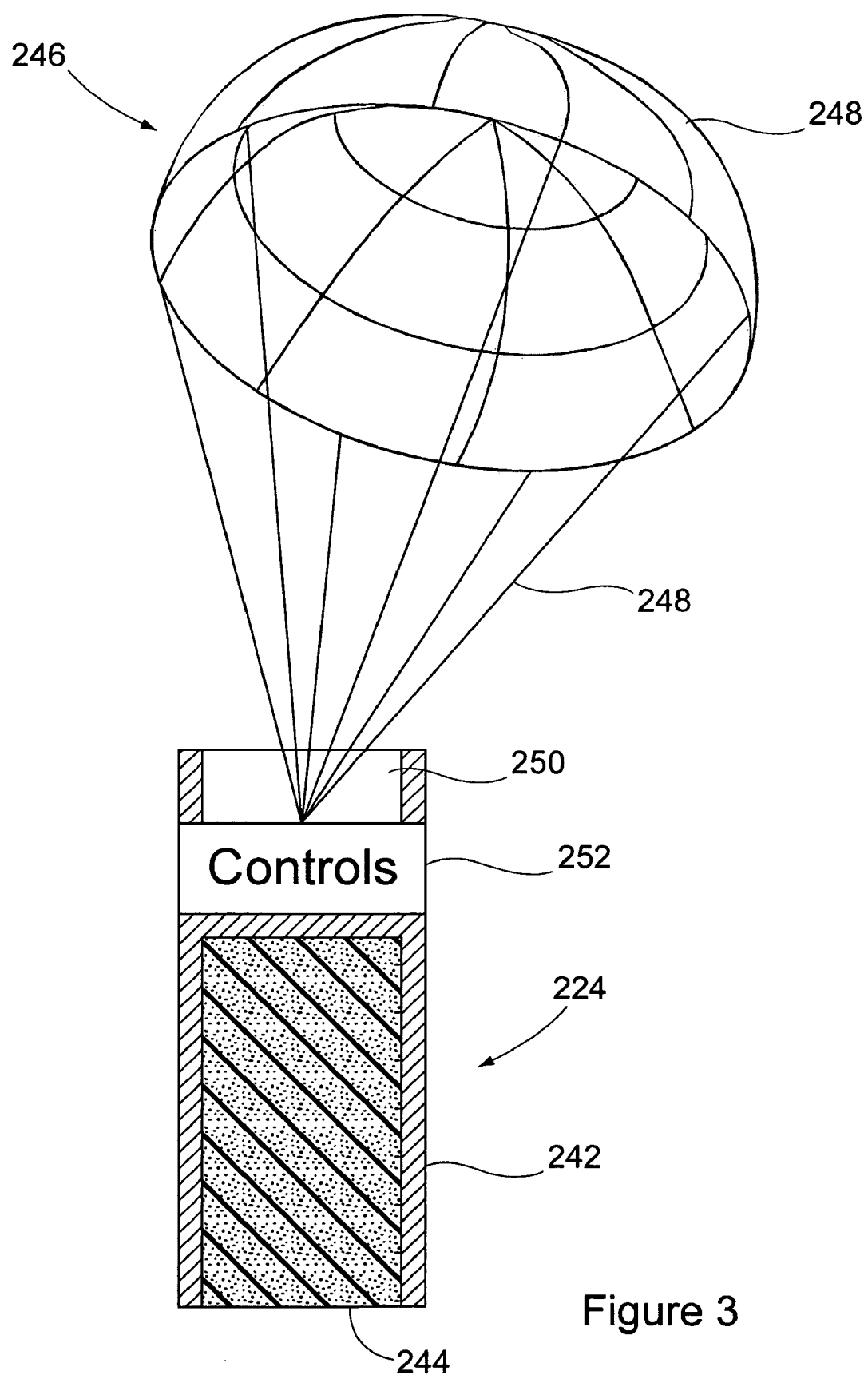
FIG. 3 illustrates a flare of another embodiment.

Turning now to FIG. 3, a flare constructed in accordance with the principles of the present disclosure is illustrated. The flare 224 shown in simplified form in FIG. 3 includes a casing (or body) 242, a candle 244, a parachute 246 which includes a canopy 248 and a plurality of risers or lines 248, a parachute compartment 250, and a control device 252. The flare 224 is shown in FIG. 3 as having been deployed with the parachute 246 open. The casing 242 contains the candle 244 which is typically a mixture of fuels, oxidizers, binding agents, stabilizers, and other chemicals. The chemicals react to produce light having a spectrum that can be tailored for a particular application by selection of the chemicals. For instance, sodium ions can be used to produce yellow light at a wavelength of about 589 nanometers. Strontium can be used to cast a red light with wavelengths at about 606 and between about 636 and 688 nanometers. Green light (with wavelengths between about 505 and 535 nanometers) can be produced by the use of barium salts while it is possible to use copper to produce a blue light (between about 420 and 460 nanometers). Other chemicals known in the art are available and can be selected for inclusion in the candle 244 to produce a desired spectrum. In addition to the candle 244, the casing usually burns as the chemicals in the candle 244 react thereby also producing light. The parachute 246, once deployed from the parachute compartment 250, serves to slow the descent of the flare 224 so that the candle 244 can burn and illuminate an area for a pre-selected time.

When the user of the system 110 (see FIG. 2) wishes to determine whether a material cloud 120 is present, the user places the detector 119 in a position from which it can view the area where the cloud 120 is suspected of being located. The user also deploys one or more clouds 114 of sensors in, and about, that area. Preferably, one or more references 128 are also deployed with the cloud 114 of sensors. At about the same time, the user deploys the flare 124 by, for example, shooting it from a flare gun (or artillery piece) or dropping it from a mobile platform (e.g. aircraft). The control system 252 (see FIG. 3) of the flare 124 causes the parachute to deploy (typically at a pre-selected altitude) and ignites the candle 244 so that the flare 126 illuminates the sensor cloud 114 as the flare 124 drifts downwardly. If the material cloud 120 is present in the volume of air that is occupied by the sensor cloud 114 then the reflectance spectrum of one or more of the sensors 126 will change to indicate the presence of the material cloud 120. Light from the flare 124 will reflect off of the sensors 126 and then to the detector 119 thereby indicating whether the material cloud 120 is present.

Flares, though, typically burn with some variation in the intensity of the light produced. The references 128 allow the system 110 to account for the variation. More particularly, the light from the flare 124 will simultaneously illuminate both the sensors 126 in the cloud 114 and the references 128. Because the references 128 can be co-deployed with the sensors 126, any variations of the light reflected from the references 128 due to non uniformities in the burning of the candle 244 can be positively identified. Thus, a determination can be made of the attenuation caused by the reaction of the sensors 126 with the material apart from the apparent attenuation caused by non uniform burning of the candle 244. Similarly, variations in the spectrum cast by the flare 124 will be accounted for by an examination of the light reflected from the reference 128. Thus, the flare 124 illuminates the sensors 126 in a manner that allows for the detection of the material cloud 120 despite environmental influences and despite variations in the composition, or burning, of the candle 244 (see FIG. 3).

Figure 4:
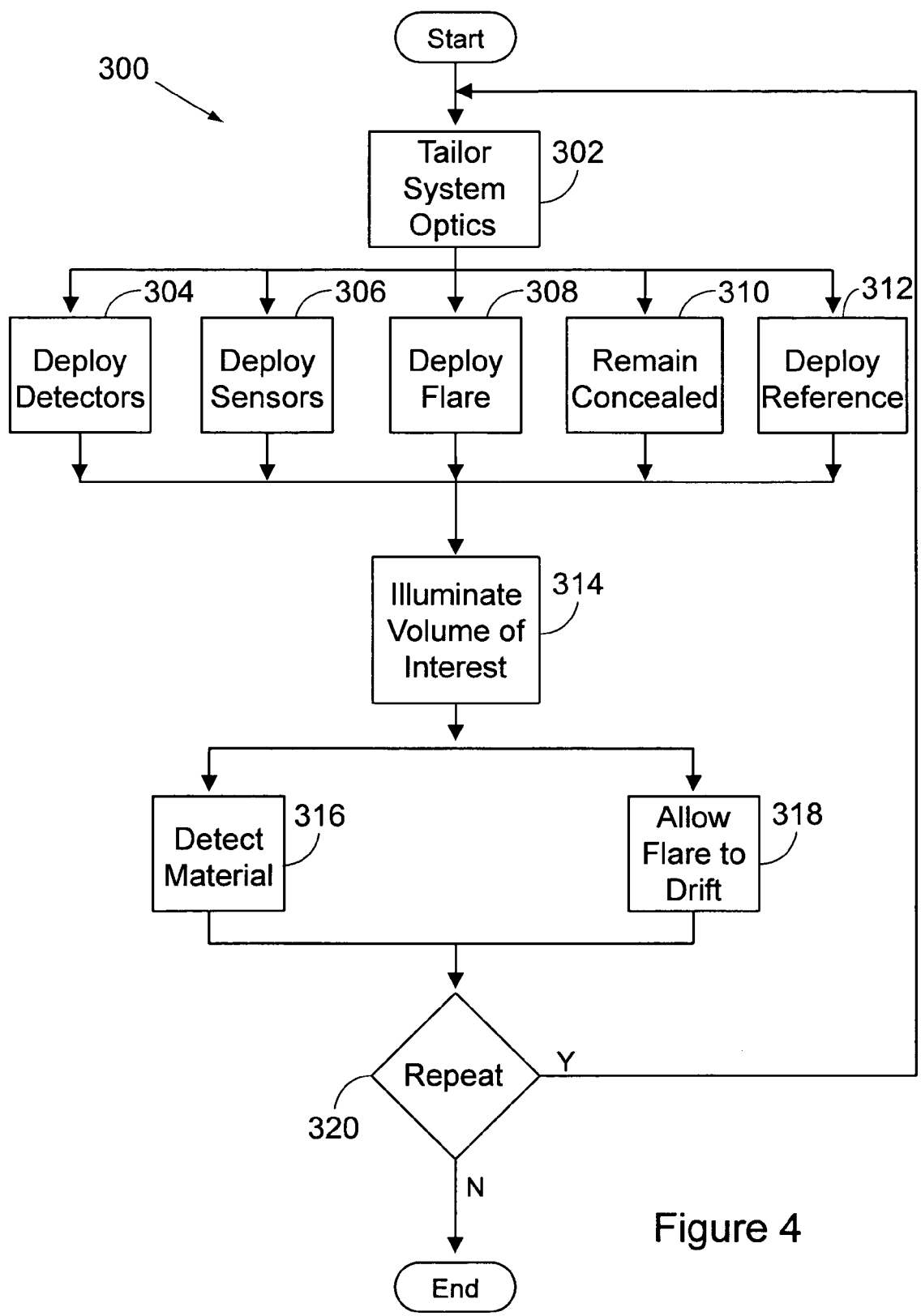
FIG. 4 illustrates a method in accordance with the principles of the present disclosure.

With reference now to FIG. 4, a method in accordance with the principles of the present disclosure is illustrated. The method 300 generally includes deploying a system to detect an airborne material and detecting the material with the system while illuminating an area with a flare. More particularly, the system may be tailored to detect a particular material. The tailoring can include selecting sensors, detectors, and flare(s) that cooperate at one or more frequencies of a spectrum to detect a given material. Further, the chemicals, or color agents, in the flare's candle can be chosen to produce a pre-selected spectrum that is tailored for the combination of the particular material a user desires to detect and the sensors the user desires to use to detect the material. See operation 302.

To begin deploying the system, the detector can be set up in an area from which it can view the area where the user wishes to detect the presence of the material, as in operation 304. The sensors are also deployed as shown by operation 306. At about that time, the flare is deployed and ignited in operation 308. Because the flare can be shot from a gun, or dropped from a plane, it is not necessary for the user to emerge from a concealed position to accomplish the deployment of the flare. See operation 310. This advantage is useful for, among other applications, detecting airborne warfare agents on a battlefield. If desired, the user can also (co) deploy one or more references to calibrate the system detector as shown by operation 312.

With the deployed flare burning and illuminating the area of interest (see operation 314), the material cloud can be detected in operation 316. Moreover because the flare is suspended from a parachute, the flare will tend to drift in parallel with the sensors and any material cloud that might be present. Thus, the combination of the flare, the sensors, and the material cloud are likely to remain within the field of view of the detector for a longer time than when other illumination sources (e.g. lasers) are used. This advantage allows the user to conserve the number of sensors and flares that would otherwise have to be deployed to maintain the ability to detect the material cloud. See operation 318. Even so, if the user desires, the user may repeat the method 300 as indicated by operation 320.

Flares allow the user to remain concealed during the deployment and use of the system. Thus, the user need not compromise a concealed position to opponents, particularly battlefield enemies. Additionally, even commercially available off the shelf flares possess sufficient optical energy and suitable spectra to enable their use in the method provided by the present disclosure. Thus, the present disclosure has provided a method of using a flare as a broadband optical source for porous silicon sensors.

The described embodiments were chosen to explain the principles of the disclosure and its practical application to enable those skilled in the art to use the disclosure in various embodiments and with various modifications as are suited to the particular use contemplated.

As various modifications could be made in the constructions and methods described and illustrated without departing from the scope of the disclosure, the description should be interpreted as illustrative rather than limiting. For example, the method of using a flare to illuminate a cloud of sensors can be practiced without using a reference. Thus, the breadth and, scope of the present disclosure should not be limited by any of the exemplary embodiments, but should be defined only in accordance with the claims.

What is claimed is:

1. A method of detecting an airborne material, comprising: deploying a cloud of optical sensors;
   illuminating at least a portion of the cloud of sensors with a flare; and
   detecting the portion of the cloud of sensors using the illumination provided by the flare.

2. The method according to claim 1, further comprising the illuminating being with at least one of infrared, near infrared, or visible electromagnetic energy.

3. The method according to claim 1, wherein the sensors are porous silicon sensors.

4. The method according to claim 1, wherein the material is a chemical agent.

5. The method according to claim 1, wherein the material is a biological agent.

6. The method according to claim 1, further comprising deploying the flare.

7. The method according to claim 6, further comprising remaining concealed while deploying the flare.

8. The method according to claim 6, further comprising selecting a detector in such a manner that the detector can detect a portion of a spectrum reflected from the sensors, the portion of the spectrum indicating whether the material is present at the sensor.

9. The method according to claim 1, further comprising comparing a spectrum of the flare with a spectrum reflected from the at least a portion of the cloud of sensors.

10. A system for detecting the presence of an airborne material, comprising:
    a plurality of optical sensors to be deployed as a cloud, each sensor to have a reflectivity that depends on whether the material is present at the sensor; and
    a flare to illuminate the optical sensors when the optical sensors are deployed as the cloud.

11. The system according to claim 10, further comprising a detector to detect the reflectivity of at least a portion of the cloud of sensors.

12. The system according to claim 10, further comprising an aircraft for deploying the flare.

13. The system according to claim 10, further comprising an artillery shell that includes the flare.

* * * * *